(12) United States Patent
Lavi et al.

(10) Patent No.: US 10,345,800 B2
(45) Date of Patent: Jul. 9, 2019

(54) ACOUSTIC MONITORING OF MACHINERY

(71) Applicant: 3D Signals Ltd., Kfar Saba (IL)

(72) Inventors: Yair Lavi, Tel Aviv (IL); Amit Ashkenazi, Hod Hasharon (IL); Ofer Affias, Hod Hasharon (IL); Amnon Shenfeld, Herzliya (IL)

(73) Assignee: 3D SIGNALS LTD., Kfar Saba (IL)

( * ) Notice: Subject to any disclaimer, the term of this patent is extended or adjusted under 35 U.S.C. 154(b) by 198 days.

(21) Appl. No.: 15/382,765

(22) Filed: Dec. 19, 2016

(65) Prior Publication Data

US 2017/0285626 A1 Oct. 5, 2017

Related U.S. Application Data

(60) Provisional application No. 62/315,032, filed on Mar. 30, 2016.

(51) Int. Cl.
*G05B 23/02* (2006.01)
*G01N 29/12* (2006.01)
(Continued)

(52) U.S. Cl.
CPC ....... *G05B 23/0289* (2013.01); *G01M 13/028* (2013.01); *G01M 15/12* (2013.01);
(Continued)

(58) Field of Classification Search
CPC .............. G05B 23/0289; G05B 23/024; G01M 13/028; G01M 15/12; G01N 29/12; G01N 29/14; G01N 29/4454; G01N 29/46
(Continued)

(56) References Cited

U.S. PATENT DOCUMENTS 5,822,212 A 10/1998 Tanaka et al.
6,173,074 B1 1/2001 Russo
(Continued)

FOREIGN PATENT DOCUMENTS

CN 101709997 A 5/2010
CN 105403730 A 3/2016
(Continued)

OTHER PUBLICATIONS

Heng, R. B. W., and Mohd Jailani Mohd Nor. Statistical analysis of sound and vibration signals for monitoring rolling element bearing condition.; Applied Acoustics; 53.1-3 (1998): 211-226. (Year: 1998).*
(Continued)

*Primary Examiner* — Mohammad Ali
*Assistant Examiner* — Joshua T Sanders
(74) *Attorney, Agent, or Firm* — Kligler & Associates

(57) ABSTRACT

Monitoring of a machine is performed by an acoustic monitor which acquires, through an acoustic sensor, acoustic signals from a vicinity of a machine, while the machine is operative. A processor calculates a frequency spectrum of a segment of the acquired acoustic signals, determines boundaries of a frequency band to be analyzed and extracts, from the calculated frequency spectrum, a base frequency window in the determined boundaries, and one or more harmonics windows of harmonics of the determined boundaries. For each of the base and harmonic windows a weight based on a distribution of values of frequencies in the windows is determined and a parameter of operation of the machine is calculated as a function of a weighted sum of the base and harmonic windows. The operation of the machine is evaluated responsive to the calculated parameter.

19 Claims, 4 Drawing Sheets

(51) Int. Cl.
  *G01N 29/44* (2006.01)
  *G01M 13/028* (2019.01)
  *G01M 15/12* (2006.01)
  *G01N 29/14* (2006.01)
  *G01N 29/46* (2006.01)

(52) U.S. Cl.
  CPC ............ *G01N 29/12* (2013.01); *G01N 29/14* (2013.01); *G01N 29/4454* (2013.01); *G01N 29/46* (2013.01); *G05B 23/024* (2013.01); *G01N 2291/2696* (2013.01); *G05B 2219/37337* (2013.01); *G05B 2219/42271* (2013.01)

(58) Field of Classification Search
  USPC .......................................................... 700/76
  See application file for complete search history.

(56) References Cited

U.S. PATENT DOCUMENTS

| | | |
|---|---|---|
| 6,507,790 B1 | 1/2003 | Radomski |
| 6,694,285 B1 | 2/2004 | Choe et al. |
| 6,778,894 B2 | 8/2004 | Beck et al. |
| 6,843,044 B2 | 1/2005 | Clauss |
| 7,752,665 B1 | 7/2010 | Robertson |
| 7,881,881 B2 | 2/2011 | Giurgiutiu et al. |
| 7,940,189 B2 | 5/2011 | Brown et al. |
| 8,554,494 B2 | 10/2013 | Adnan et al. |
| 8,595,831 B2 | 11/2013 | Skare |
| 8,600,627 B2 | 12/2013 | Beck |
| 8,607,093 B2 | 12/2013 | Dehaan et al. |
| 8,903,558 B2 | 12/2014 | Jarrell et al. |
| 8,919,231 B2 | 12/2014 | Butler et al. |
| 8,964,995 B2 | 2/2015 | Cohn et al. |
| 8,983,677 B2 | 3/2015 | Wright et al. |
| 9,342,695 B2 | 5/2016 | Barkan |
| 9,378,455 B2 | 6/2016 | Yufik |
| 9,401,932 B2 | 7/2016 | Deerman et al. |
| 9,945,755 B2 | 4/2018 | Pluemer |
| 9,971,667 B1 | 5/2018 | Jenkins et al. |
| 9,989,439 B2 * | 6/2018 | Thomson ............ G01M 13/045 |
| 2002/0020561 A1 | 2/2002 | Alft et al. |
| 2002/0091491 A1 | 7/2002 | Jackson et al. |
| 2002/0194915 A1 | 12/2002 | Abdel-Malek et al. |
| 2004/0117050 A1 | 6/2004 | Oskin et al. |
| 2008/0271143 A1 | 10/2008 | Stephens et al. |
| 2008/0276111 A1 | 11/2008 | Jacoby et al. |
| 2008/0282781 A1 | 11/2008 | Hemblade |
| 2010/0126258 A1 * | 5/2010 | Beck ........................ A01F 29/22 |
| | | 73/104 |
| 2011/0301882 A1 | 12/2011 | Andersen |
| 2011/0320139 A1 | 12/2011 | Amir et al. |
| 2013/0211558 A1 | 8/2013 | Mishina et al. |
| 2014/0195184 A1 | 7/2014 | Maeda et al. |
| 2014/0244192 A1 | 8/2014 | Craig et al. |
| 2014/0298399 A1 | 10/2014 | Heo et al. |
| 2015/0317475 A1 | 11/2015 | Aguayo Gonzalez et al. |
| 2015/0346706 A1 | 12/2015 | Gendelman et al. |
| 2016/0004225 A1 | 1/2016 | Ellwein |
| 2016/0117503 A1 | 4/2016 | Reed et al. |
| 2016/0117905 A1 | 4/2016 | Powley et al. |
| 2016/0234235 A1 | 8/2016 | Jover et al. |
| 2016/0275289 A1 | 9/2016 | Sethumadhavan et al. |
| 2016/0277423 A1 | 9/2016 | Apostolescu et al. |

FOREIGN PATENT DOCUMENTS

| | | |
|---|---|---|
| DE | 3907419 A1 | 9/1990 |
| EP | 0317322 A2 | 5/1989 |
| EP | 3015866 A1 | 5/2016 |
| KR | 101587827 B1 | 1/2016 |
| WO | 0171362 A1 | 9/2000 |
| WO | 2008142386 A1 | 11/2008 |
| WO | 2015102730 A2 | 7/2015 |
| WO | 2016115280 A1 | 7/2016 |

OTHER PUBLICATIONS

Microsoft Computer Dictionary, Fifth Edition; Microsoft Press; (2002); p. 133 ISBN:0735614954 (Year: 2002).*
International Application # PCT/IB2016/057776 Search Report dated Apr. 20, 2017.
U.S. Appl. No. 15/385,978 office action dated Dec. 17, 2018.
Leclere et al., "A multi-order probabilistic approach for Instantaneous Angular Speed tracking debriefing of the CMMNO14 diagnosis contest", Mechanical Systems and Signal Processing 81, pp. 1-23, Mar. 24, 2016.
Microsoft Computer Dictionary, fifth edition, Microsoft Press, p. 133, year 2002.
Heng et al., "Statistical analysis of sound and vibration signals for monitoring rolling element bearing condition", Applied Acoustics, vol. 53, Issues 1-3, pp. 211-226, Jan.-Mar. 1998.

* cited by examiner

ACOUSTIC MONITORING OF MACHINERY

RELATED APPLICATIONS

The present application claims the benefit of U.S. provisional patent application 62/315,032, filed Mar. 30, 2016, the disclosure of which is incorporated herein by reference in its entirety.

TECHNICAL FIELD

Embodiments described herein relate generally to machinery monitoring, and particularly to methods and systems for acoustic monitoring of machinery.

BACKGROUND

Various techniques for monitoring machinery are known in the art. Some methods, such as described, for example, in PCT publication WO 01/71362 or U.S. Pat. No. 6,694,285 to Choe, are based on measurement of mechanical vibrations.

Other methods are based on sensing of acoustic signals from the machinery. These methods do not require physical coupling of sensors to monitored machinery.

US patent publication 2016/0117905 to Powley, describes comparing environment sounds to predetermined signatures to identify events occurring in the environment.

U.S. Pat. No. 6,507,790 to Radomski, titled "Acoustic Monitor", describes monitoring the sound from rotating or non-rotating machinery and comparing the monitored sounds to those collected in a learn mode.

U.S. Pat. No. 8,903,558 to Jarrell et al., titled Monitoring Pipeline Integrity, describes the use of a microphone to sense acoustic sound signals from a monitored pipeline. The sensed signals are compared to previously acquired baseline signals to detect threat conditions.

U.S. Pat. No. 8,607,093 to DeHaan et al., titled "Systems and methods for detecting machine faults in network using acoustic monitoring", describes detecting machine faults in a network using acoustic monitoring. Acoustic data from near a subject machine is analyzed using spectral analysis. Monitored acoustic data is compared to acoustic profiles of malfunction components or other anomalous conditions. One example given by DeHaan relates to identification of a bearing whine of a failed hard disk.

US patent publication 2002/0020561 to Alft et al., titled "Real-time control system and method for controlling an underground boring machine", describes comparing signals from a boring machine to an acoustic profile of the machine developed empirically.

European patent application 3 015 866 to ABB Technology AG, titled: "A method of automatic determination of rotational speed of a shaft in a rotating machine", describes generating a tone of known frequency in proximity to a shaft, recording acoustic signals responsive to the generated tone and accordingly determining a speed of the shaft.

In many cases, acoustic signals suffer from high levels of noise which may interfere with comparison of acoustic signals.

U.S. Pat. No. 6,778,894 to Beck et al. describes monitoring acoustic noise signal collected by a microphone from a working vehicle. This patent suggests determining a parameter from the signal, in particular the frequency and/or amplitude of vibration.

SUMMARY

There is provided in accordance with an embodiment of the present invention, a method of monitoring a machine, including acquiring, by an acoustic sensor, acoustic signals from a vicinity of a machine, while the machine is operative, calculating, by a processor, a frequency spectrum of a segment of the acquired acoustic signals, determining boundaries of a frequency band to be analyzed, extracting, from the calculated frequency spectrum, a base frequency window in the determined boundaries, and one or more harmonics windows of harmonics of the determined boundaries, determining for each of the base and harmonic windows a weight based on a distribution of values of frequencies in the windows, calculating a parameter of operation of the machine as a function of a weighted sum of the base and harmonic windows and evaluating operation of the machine, responsive to the calculated parameter.

Optionally, the method includes generating an alert, responsive to a determination that the calculated parameter is outside a predefined range of values for the parameter. Optionally, the method includes generating an alert, responsive to a determination that the calculated parameter is different than a corresponding value reported by a controller of the machine. Optionally, calculating the operation parameter comprises determining a frequency in the weighted sum of the windows having a maximal power.

Optionally, calculating the operation parameter comprises determining a ratio between power in a segment around a given frequency in the weighted sum of the windows and a measure of power outside the segment. Optionally, determining a weight for each window comprises determining a frequency-domain entropy of the window. Optionally, evaluating operation of the machine comprises determining a time until a required maintenance of the machine, as a function of the calculated parameter.

Optionally, the method includes automatically changing an operation state of the machine responsive to the evaluation. Optionally, acquiring the acoustic signals comprises acquiring by an acoustic sensor monitor including the processor, wherein the acoustic sensor monitor is not connected to the controller, such that data and instructions cannot pass from the controller to the monitor.

There is further provided in accordance with an embodiment of the present invention an acoustic machine monitor, comprising an acoustic sensor for acquiring acoustic signals from a vicinity of a machine, while the machine is operative; and a processor configured to calculate a frequency spectrum of a segment of the acquired acoustic signals, to determine boundaries of a frequency band to be analyzed, to extract from the calculated frequency spectrum, a base frequency window in the determined boundaries, and one or more harmonics windows of harmonics of the determined boundaries, to determine for each of the base and harmonic windows a weight based on a distribution of values of frequencies in the windows, to calculate a parameter of operation of the machine as a function of a weighted sum of the base and harmonic windows, and to evaluate operation of the machine, responsive to the calculated parameter.

The processor is optionally configured to generate an alert, responsive to a determination that the calculated parameter is outside a predefined range of values for the parameter.

There is further provided in accordance with an embodiment of the present invention a method of monitoring a machine, comprising acquiring, by an acoustic sensor, acoustic signals from a vicinity of a machine, while the machine is operative, calculating, by a processor, a frequency spectrum of a segment of the acquired acoustic signals, calculating a ratio between power in one or more frequency segments of the frequency spectrum and a power of the frequency spectrum at least in the frequencies outside the one or more segments and evaluating operation of the machine, responsive to the calculated ratio.

Optionally, calculating the ratio comprises calculating a numerator of the ratio as a power in frequency segments around an operation frequency of the machine and one or more harmonics of the operation frequency. Optionally, the operation frequency comprises a frequency corresponding to a time period of a single cog of a gear of the machine. Optionally, evaluating operation of the machine comprises automatically providing an estimate of a time to a required replacement of the gear.

Optionally, the operation frequency comprises a frequency corresponding to an entire cycle of a gear of the machine. Optionally, evaluating operation of the machine comprises determining that the ratio is in a predetermined range and providing an alert of a broken gear cog responsively to the determining.

Optionally, calculating the ratio comprises calculating a denominator of the ratio as a power of the entire frequency spectrum.

Optionally, calculating the ratio comprises calculating a denominator of the ratio as a power of the frequency spectrum not included in the segments.

Optionally, calculating the frequency spectrum comprises extracting a sample of a given duration from the acquired signals and calculating the frequency spectrum from the extracted sample. Optionally, extracting the sample comprises extracting at times defined by an electrical timing signal from the machine.

These and other embodiments will be more fully understood from the following detailed description of the embodiments thereof, taken together with the drawings in which:

DETAILED DESCRIPTION OF EMBODIMENTS

Overview

An aspect of some embodiments of the present invention relates to apparatus for acoustically monitoring a machine, which calculates one or more operation parameters of the machine from acoustic signals passively collected from the machine. In order to overcome problems of noise, the apparatus calculates the one or more operation parameters, e.g., a fundamental frequency of the machine operation, from a weighted sum of a plurality of harmonics of frequency bands known to include an operation frequency of the machine. The weights are optionally functions of entropy values of the windows. Weighing the harmonic frequency bands by functions of the entropy values allows for use of a plurality of harmonic windows from a noisy environment, without more noisy harmonic frequency bands masking out data from less noisy frequency bands.

An aspect of some embodiments of the present invention relates to apparatus for acoustically monitoring a machine, which evaluates the machine operation based on a sharpness of the operation frequency of the machine relative to surrounding frequencies in a frequency window. The sharpness is indicative of the operation of the machine and is optionally used to indicate when maintenance, such as part replacement, is required.

In some embodiments of the invention, the acoustic monitoring is performed on time samples extracted from an acoustic signal collected from the vicinity of the machine. Optionally, the timing of the extracted sample is determined from a gating signal received from the machine, indicating beginning and/or ending of machine operation.

System Description

Figure 1:
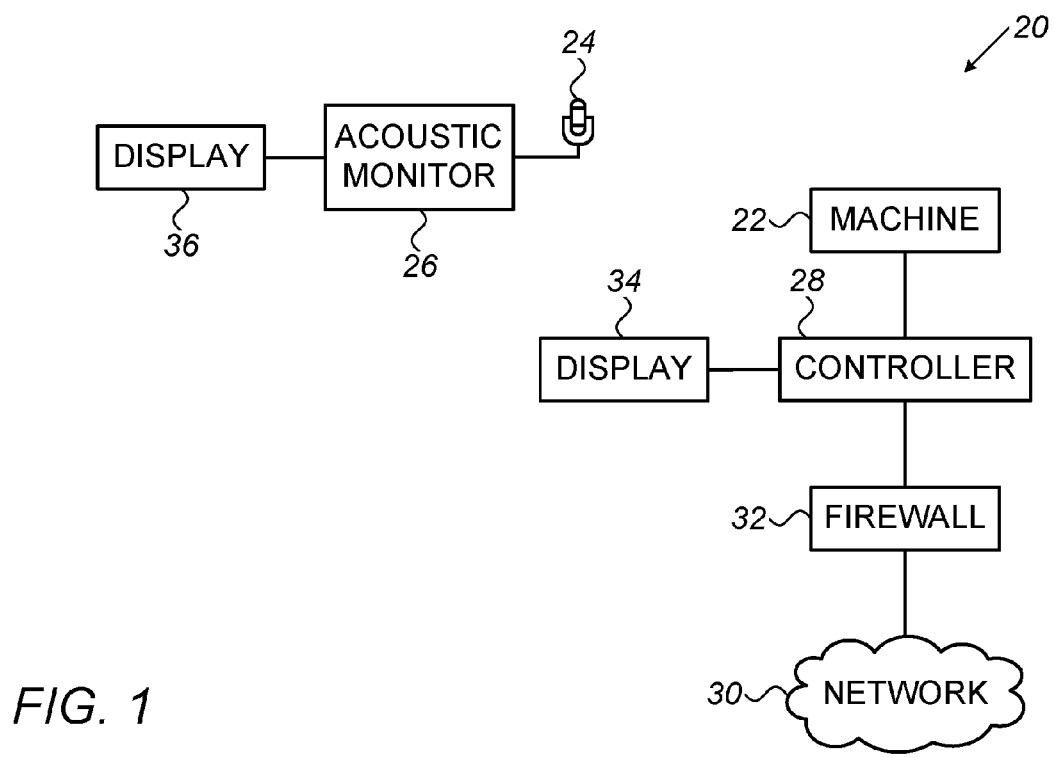
FIG. 1 is a block diagram that schematically illustrates a machine system including acoustic monitoring, in accordance with an embodiment of the invention.

FIG. 1 is a block diagram that schematically illustrates a machine system 20 including acoustic monitoring of a machine 22, in accordance with an embodiment of the invention. In addition to machine 22, machine system 20 includes a microphone 24 and an acoustic signal monitor 26, which analyses acoustic signals collected by microphone 24 from machine 22, in order to monitor the operation of the machine. In some embodiments, a controller 28 controls the operation of machine 22. Optionally, controller 28 is connected to a communication network 30, such as the Internet, through which operation commands for machine 22 are received from a remote user. A firewall 32 optionally protects controller 28 from unauthorized, possibly malicious, instructions. In some embodiments, a controller display coupled to controller 28, provides feedback on the operation of machine 22. Alternatively or additionally, feedback on the operation of machine 22 is provided to a remote user, through communication network 30. Optionally, a separate display 36, referred herein as monitor display 36, is coupled to acoustic monitor 26 and provides output from monitor 26. Alternatively or additionally, audio output is provided from monitor 26.

Optionally, microphone 24 and acoustic signal monitor 26 are not coupled to machine 22 and/or controller 28. Accordingly, acoustic signal monitor 26 monitors the operation of machine 22 independent of controller 28. Independent feedback on the operation of machine 22, provided by acoustic signal monitor 26, serves as a sanity check for controller 28.

Alternatively to acoustic signal monitor 26 being completely decoupled from machine 22 and controller 28, acoustic signal monitor 26 is coupled to controller 28 in a manner allowing for limited transfer of information. In some embodiments, acoustic signal monitor 26 does not receive any information from controller 28. In other embodiments, acoustic signal monitor 26 receives from controller 28 parameter values of the operation of machine 22 and uses these parameter values only to compare them to self-determined values of the parameters, as discussed hereinbelow. In these embodiments, the coupling between acoustic signal monitor 26 and controller 28 only allows flow of specific information from controller 28 to acoustic signal monitor 26. Alternatively or additionally, acoustic signal monitor 26 is coupled to controller 28 in a manner allowing submission of emergency instructions, in case a problem requiring immediate intervention is detected. Possibly, a one way link physically limiting passage of signals in only one direction is used in coupling acoustic signal monitor 26 and controller 28.

Machine 22 may be any machine which generates noise during operation, such as pumps, motors, rotating saws and turbines. Machine 22 optionally, repeatedly performs specific tasks, generating a repetitive acoustic signal. Optionally, machine 22 includes one or more rotating elements, such as a shaft, bearing, gear or rotating blade, which generate acoustic signals during rotation.

Microphone 24 is designed to collect acoustic signals in a frequency band including the acoustic signals generated by the operation of machine 22. Microphone 24 optionally collects sonic and ultrasonic signals. Optionally, microphone 24 collects the acoustic signals passively without transmitting any activation signals. Microphone 24 typically includes a power source, an amplifier and an analog to digital converter (ADC) and supplies digital signals. In some embodiments, machine system 20 comprises a plurality of microphones, for noise cancellation.

Acoustic signal monitor 26 may be located adjacent microphone 24 or may be remote from microphone 24 and communicate with the microphone 24 through a wire and/or wireless communication link.

In some embodiments, acoustic signal monitor 26 comprises a programmable processor capable of executing software for carrying out the functions described herein. The software may be downloaded to the processor in electronic form, over a network, for example, or it may, alternatively or additionally, be provided and/or stored on non-transitory tangible media, such as magnetic, optical, or electronic memory. Alternatively or additionally, acoustic signal monitor 26 comprises dedicated hardware and/or firmware which carry out some or all of the tasks of monitor 26.

Figure 2:
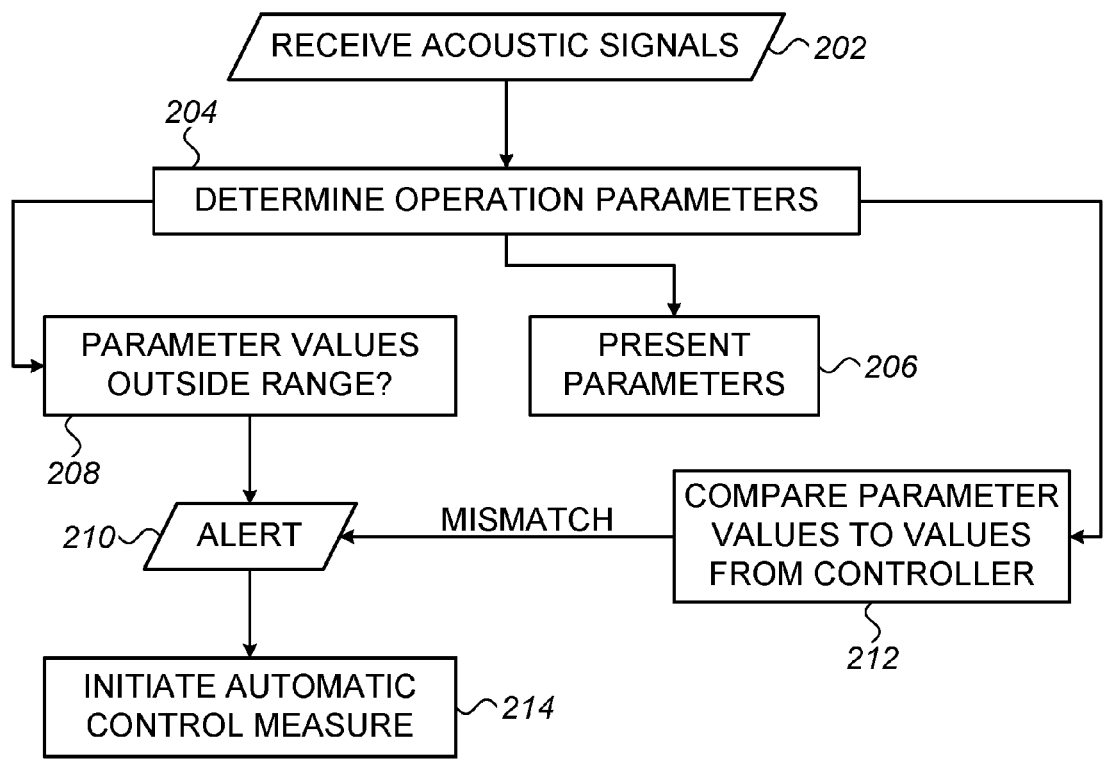
FIG. 2 is a flowchart of acts performed by an acoustic signal monitor, in accordance with an embodiment of the invention.

FIG. 2 is a flowchart of acts performed by acoustic signal monitor 26, in accordance with an embodiment of the invention. Monitor 26 receives (202) acoustic signals collected by microphone 24. Values of one or more parameters of the operation of machine 22 are determined (204) from the received acoustic signals. The determined parameter values are presented (206) to a human operator, who can determine accordingly whether machine 22 is operating properly. Alternatively or additionally, acoustic signal monitor 26 is configured with expected values or value ranges (e.g., upper and/or lower thresholds) of the parameters. In this alternative, if the value of a parameter is determined (208) to be outside a corresponding expected range, an alert is generated (210). Further alternatively or additionally, acoustic signal monitor 26 receives feedback on the operation of machine 22 from controller 28 and compares (212) the feedback to the parameters determined by acoustic signal monitor 26. If a mismatch is found, an alert is provided (210).

In some embodiments, the alert is provided (210) to a human operator. Alternatively or additionally, automatic operations are initiated (214) in response to the alert. The automatic operations may include, for example, a shutdown of machine 22, or a change in its operation parameters. In some embodiments, the automatic operations may include further tests.

The automatic operations are optionally selected in response to the specific parameter values determined. For example, when a parameter has a value which is outside a prescribed range by a large extent, an immediate automatic intervention is performed, while if the discrepancy of the value is small, further tests are performed.

Alternatively to acoustic signal monitor 26 relating only to acoustic signals, monitor 26 scans information from additional sources and makes decisions on providing alerts based on the information from the plurality of sources.

The acts of the method of FIG. 2 may be carried out in response to a user instruction, or according to a predetermined schedule, such as once an hour or once a day. Alternatively, the acts are carried out continuously, for example every second or every minute. In some embodiments, monitor 26 repeatedly registers the values of one or more parameters over time and presents a rate of change of the parameter and/or evaluates machine 22 based on the rate of change. For example, an increased rate of change of signal distinction and/or of a regularity parameter may be indicative of increased wear in machine 22 caused by a problem in machine 22 and/or controller 28.

Monitor 26 may determine various machine operation parameter values, including a machine operation frequency, an acoustic signal distinction, regularity parameter and operation ratio parameter. Examples of methods for determining the values of these parameters are discussed below with relation to FIGS. 3-7.

Other values which are monitored by monitor 26, in some embodiments, include total acoustic amplitude or power and/or acoustic amplitude or power of one or more frequency bands.

Figure 3:
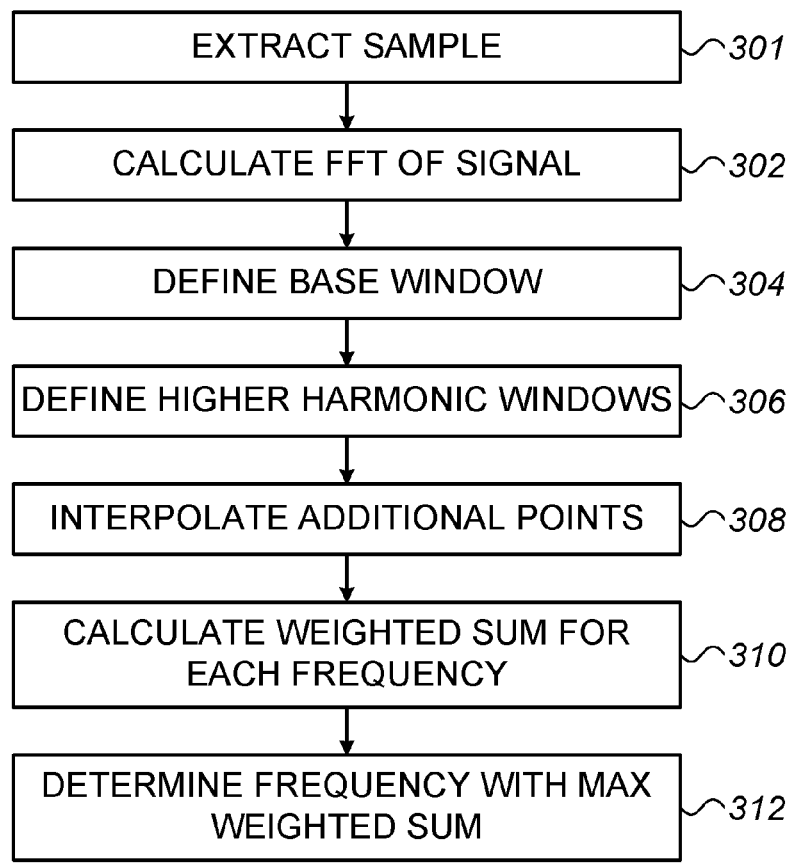
FIG. 3 is a flowchart of a method for determining a machine operation frequency, in accordance with an embodiment of the invention.

FIG. 3 is a flowchart of a method for determining a machine operation frequency, in accordance with an embodiment of the invention. Optionally, a sample for analysis is extracted (301) from the acoustic signals collected by microphone 24 and a frequency spectrum of the sample is calculated (302), for example by a Fast Fourier transform (FFT). The frequency spectrum optionally states an acoustic amplitude for each frequency.

A base frequency window expected to include a frequency of repetitive operation of machine 22 is defined (304) and corresponding frequency windows of higher harmonics of the base frequency window are also defined (306). For example, if the repetitive operation frequency of machine 22 is known to be between 300-1000, a base window is defined to include the frequencies of the FFT in this range. A second harmonic window is defined between 600-2000 Hz, a third harmonic window is defined between 900-3000 Hz, etc. In this example, the different harmonic windows overlap. This is not necessary, and in other cases a much narrower window is defined (e.g., 50-60 Hz) and the harmonics (e.g., 100-120, 150-180, 200-240 Hz, 250-300 Hz) do not overlap.

In some embodiments, for ease of further calculations, the number of data points in each of the frequency windows is equalized, by interpolating (308) additional points based on the available values in the windows and/or by removing excess data points.

For each frequency in the base window, a weighted sum of the power of the corresponding harmonics is calculated (310). The frequency with the maximal weighted power sum is determined (312) as the repetitive operation frequency of machine 22.

Optionally, the weights of the harmonic windows used in the weighted sum reflect an extent to which the window is noise-free and has distinct information in specific frequencies. In some embodiments, the weight of each harmonic window is calculated as:

$$W_i = 1 - \frac{H_i}{\log(n)}$$

where Hi is the frequency-domain entropy of the frequency distribution in the window of harmonic i and n is the number of samples in the window.

The machine operation frequency ω is optionally determined (312) as $$\omega = \underset{v}{\operatorname{argmax}} \sum_{n=1}^{k} [(f^2(nv)] * W_i)$$

in which k is the number of harmonics taken into consideration, v is considered over the frequencies in the base window and f is the absolute value of the Fourier transform of the signal.

By using weights which are dependent on frequency-domain entropy of the windows, the information from many harmonic windows can be used, without noisy windows masking out the useful information. Alternatively, other weights $W_i$ reflecting the distinctiveness of data in each window, are used. For example, in some embodiments, a periodicity shape of the frequencies in a normal mode of operating of machine 22 is determined. Frequencies known to have a higher frequency in the normal mode of operation are optionally assigned a corresponding larger weight $W_i$.

The extracted (301) sample optionally has a length of between about 0.1-30 seconds, possibly between 1-5 seconds. It is noted, however, that in some embodiments, a shorter sampling period of less than 1 second, less than 0.1 second or even less than 5 milliseconds is used. In other embodiments, a longer sampling period, for example at least 30 seconds, at least 2 minutes or even at least 10 minutes is used.

In some embodiments, acoustic signals are continuously received through microphone 24 and acoustic signal monitor 26 extracts samples of a desired length from the received acoustic signals. Optionally, the samples are extracted beginning at arbitrary time points. Alternatively, for example for machines which alternate between different states of operation with different noise spectrums, acoustic signal monitor 26 identifies transitions between operation states and extracts samples which were acquired during a single operation state. In some embodiments, the beginning of extracted samples is immediately after an identified transition to increase the chances that the sample is entirely within a single operation state.

For example, when machine 22 comprises a cutting machine, the machine operates in an idle state in which a cutter rotates without coming in contact with an element to be cut, and a cutting state in which the element being cut is brought in contact with the cutter. The analysis of the cutting machine is performed separately for the different states or only for the cutting state.

In some embodiments, the machine operation state is received as an electrical gating signal from the machine. Alternatively, the machine operation state is determined from the received acoustic signals. Optionally, the machine operation state is determined from the acoustic signals by identifying a characteristic background noise of different machine states and accordingly classifying current signals. Alternatively or additionally, the machine operation state is determined by identifying a transition noise, such as a clamping performed before a cutting session begins.

Referring in detail to defining (304) a frequency window expected to include the operation frequency of machine 22, in some embodiments of the invention the window is defined by a human operator of acoustic signal monitor 26. Optionally, the human operator indicates an expected operation frequency and monitor 26 automatically defines a range around the indicated expected operation frequency to be included in the window. The range optionally includes a percentage of the frequency, for example, 10% or 15%, or a predefined frequency range, e.g., ±50 Hz or ±100 Hz.

In some embodiments, monitor 26 performs a preliminary analysis of the acquired signals and accordingly selects the frequency window. Optionally, monitor 26 determines a first maxima of the frequency spectrum of the sample and defines a range around the first maxima frequency. Alternatively, monitor 26 selects a window around a predetermined number of first maxima in the frequency spectrum. Further alternatively, monitor 26 determines one or more first maxima for a plurality of samples and accordingly defines the frequency window, for example one that encompasses the first maxima in all the samples or in most of the samples.

In some cases, monitor 26 defines a plurality of different frequency windows and repeats the method of FIG. 3 for each of the defined windows. The results are displayed to an operator for each of the frequency windows or the window with a most distinct calculated weighted sum is chosen.

Referring in more detail to defining (306) the harmonic windows, in some embodiments, at least 2 additional harmonic windows are defined. In other embodiments, at least 4 additional harmonic windows are defined. In some embodiments, the number of harmonic windows used depends on the frequency range of the base window. Alternatively or additionally, the number of harmonic windows used depends on a measure of signal quality in the harmonic windows. Optionally, a quality measure is defined for each window beyond a predetermined number of first harmonics and harmonics beyond a harmonic window having a quality value below than a predetermined threshold are not taken into consideration. The quality measure optionally is a function of the frequency-domain entropy of the frequency distribution in the window. Alternatively or additionally, the quality measure optionally is a function of the total power of the frequencies in the window. Windows having a power lower than a low threshold and/or higher than a high threshold are optionally considered of low quality.

Figure 4:
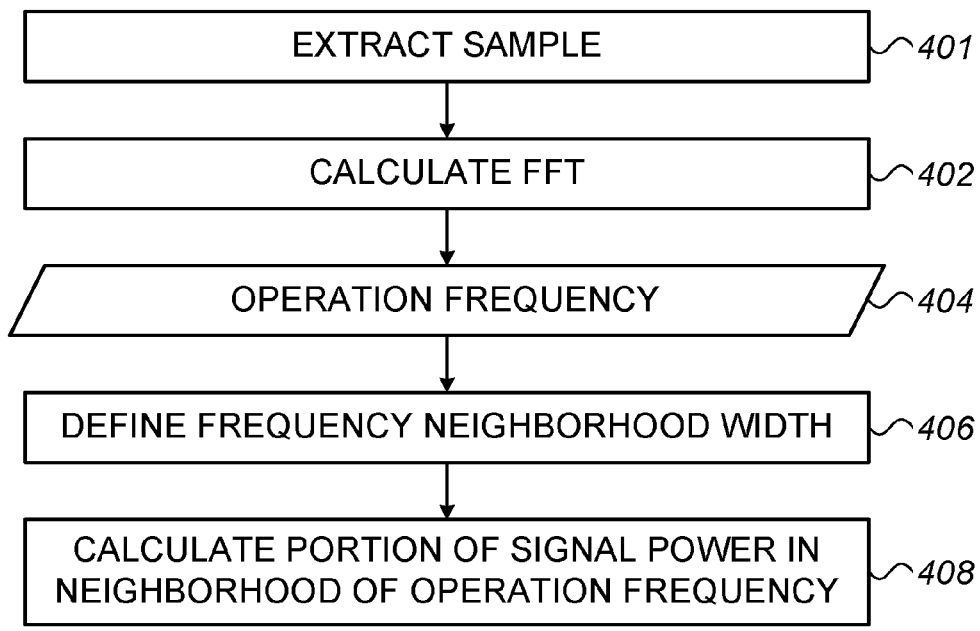
FIG. 4 is a flowchart of a method for determining a value of a signal distinction parameter, in accordance with an embodiment of the invention.

FIG. 4 is a flowchart of a method for determining a value of a signal distinction parameter, in accordance with an embodiment of the invention. Optionally, a sample for analysis is extracted (401) from the acoustic signals collected by microphone 24, using any of the methods described above with reference to FIG. 3, and a frequency spectrum of the collected signals is calculated (402), for example by a Fast Fourier transform (FFT). An estimate of the operation frequency of the machine, is received (404). Additionally, a frequency neighborhood width, indicating a width around a specific frequency that is to be considered related to the specific frequency, is defined (406). A measure of a portion of the power of the sample that is within a limited band around the received operation frequency, and optionally one or more of its additional harmonics, is calculated (408), and serves as the signal distinction parameter.

In one embodiment, the signal distinction parameter (SDP) is calculated using the formula:

$$SDP = \frac{\sum_{n=1}^{k} \sum_{m=-j}^{j} f^2(n\omega + m*d\omega)}{\sum_{n=1}^{k} \sum_{m=-l}^{l} f^2(n\omega + m*d\omega) - \sum_{n=1}^{k} \sum_{m=-j}^{j} f^2(n\omega + m*d\omega)}$$

in which f( ) is the absolute value of the FFT of the acoustic signal, ω is the received operation frequency, k is the number of harmonic windows being used in the calculations and dω is the frequency resolution of the FFT. The defined (406) frequency neighborhood width is represented by j, and l defines the entire width of the harmonic windows.

In other embodiments, the values of the various harmonic windows are weighted, for example as discussed above regarding the method of FIG. 3.

It is noted that in the above equation, the portion of the power of the acoustic signal in the limited band around the operation frequency is divided by the power of the remaining parts of the acoustic signals. In other embodiments, the portion of the power of the acoustic signal in the limited band around the operation frequency is divided by the power of the entire signal, such as using the equation:

$$SDP = \frac{\sum_{n=1}^{k} \sum_{m=-j}^{j} f^2(n\omega + m*d\omega)}{\sum_{n=1}^{k} \sum_{m=-l}^{l} f^2(n\omega + m*d\omega)}$$

The number of harmonic windows k is optionally between about 2-6 harmonics. The number of harmonics considered optionally depends on the quality of the acoustic signal and/or the frequency spectrum of the acoustic signals from the machine. Any of the methods for selecting the number of harmonics considered described above with reference to FIG. 3 may be used in the method of FIG. 4.

Various methods may be used to define (406) the frequency neighborhood width j*dω. In some embodiments, the frequency neighborhood width has a predetermined system-configured value and/or is configurable by the user. In other embodiments, the frequency neighborhood width is set based on test measurements performed on machines similar to machine 22 and/or based on old test measurements on machine 22. For example, the frequency neighborhood width may be selected to achieve for the test measurements a signal distinction parameter of a specific value (e.g., 50%). Optionally, the frequency neighborhood width j*dω is smaller than 250 Hz or even less than 100 Hz. Optionally, the frequency neighborhood width j*dω is between about 10-100 Hz. In some embodiments, the parameter is calculated for a plurality of different frequency neighborhood width values.

Alternatively, the signal distinction parameter is calculated as a frequency neighborhood width for which the neighborhood band of the received operation frequency includes a given percentage of the signal power.

Further alternatively or additionally, the signal distinction parameter is calculated as a ratio between the signal at the received operation frequency and the signal at a given distance from the received operation frequency.

In some embodiments, the received (404) operation frequency of the machine, is a user provided value. Alternatively, the received (404) operation frequency of the machine is calculated from the same acoustic signal used in calculating the value of the signal distinction parameter, for example using the method of FIG. 3. Further alternatively, the received (404) operation frequency of the machine is calculated from a different acoustic sample than used in calculating the value of the signal distinction parameter.

Applicant has determined that in machines based on rotating elements (e.g., gears), the signal distinction parameter (SDP) is generally dependent on the state of the gears. The rate of change of the signal distinction parameter is generally representative of the rate of eroding of the gears. Monitor 26 can thus indicate when the gears should be replaced and can point out a problem with machine 22 causing faster than expected gear eroding.

Figure 5A:
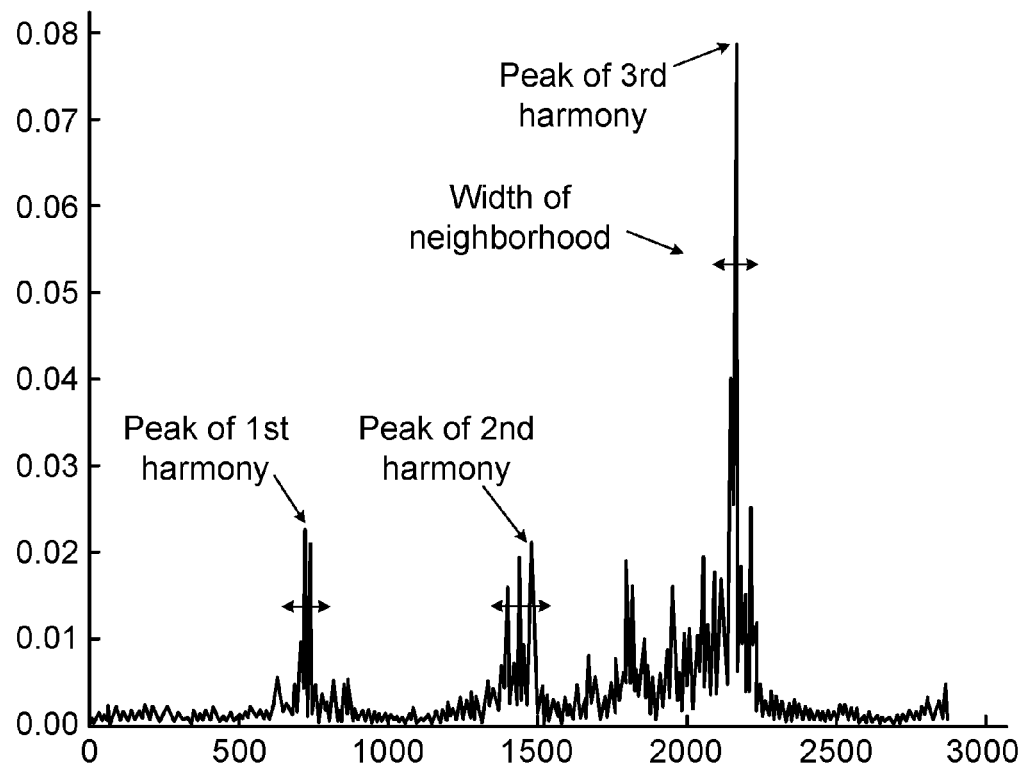
FIGS. 5A and 5B are graphs showing typical spectrums of a machine with non-broken teeth and of a machine with broken teeth, respectively, as determined in accordance with embodiments of the present invention.
Figure 5B:
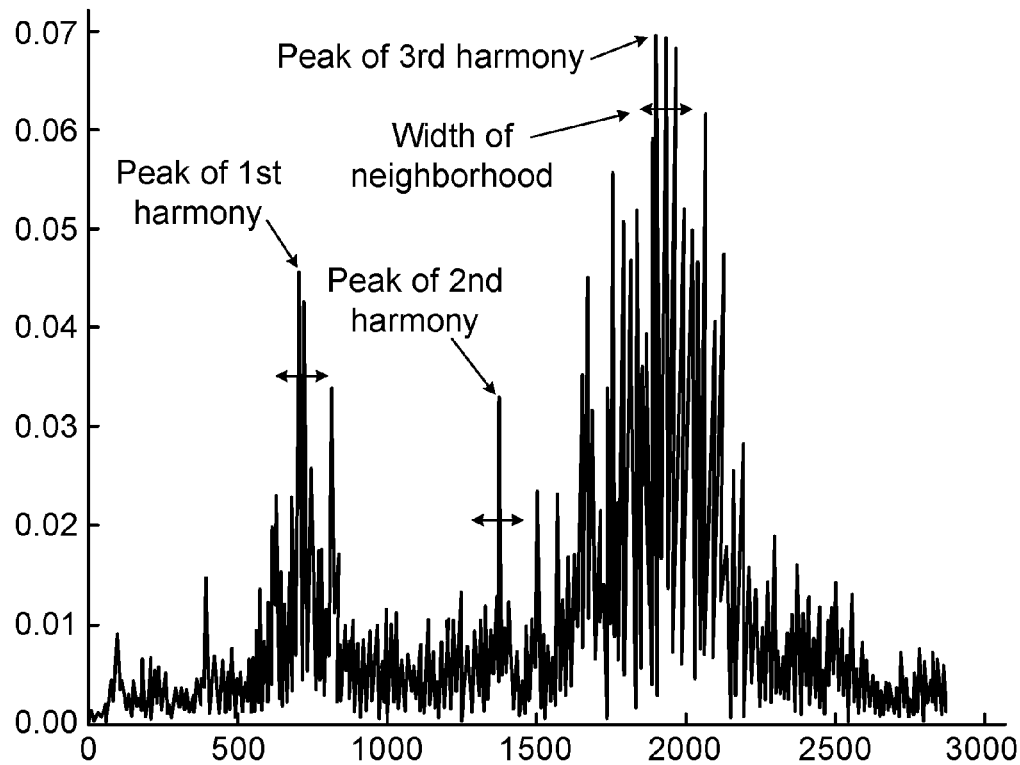

FIGS. 5A and 5B are graphs showing typical spectrums of a machine with non-broken teeth and of a machine with broken teeth, respectively, as determined in accordance with embodiments of the present invention.

In FIG. 5A, the first and third harmonics show very distinct peaks and even the second harmonic has most of its energy concentrated around its peak. Accordingly, the calculated signal distinction parameter (SDP) is relatively high and indicative of healthy teeth of the gears of machine 22. In FIG. 5B, in contrast, a substantial amount of the power of the signal is not in the surroundings of the harmonic peaks and therefore the calculated SDP is lower. This is indicative of a degrading of the gears of machine 22.

In some embodiments of the invention, the value of SDP is displayed to a human operator. Alternatively or additionally, when the SDP value is below a preconfigured threshold value a notice to replace a gear of machine 22 is provided to the operator. In some embodiments, the rate of change of the SDP value is monitored and/or displayed to the operator.

Alternatively or additionally to calculating the SDP around an operation frequency of machine 22 which is an inverse of a period of a single tooth (or cog) of a gear of the machine, the SDP is calculated around a cycle frequency of an entire cycle of the gear. A high SDP value for this frequency is indicative of existence of a noise generated at the cycle frequency, which is probably due to one or more broken teeth of the gear.

Figure 6:
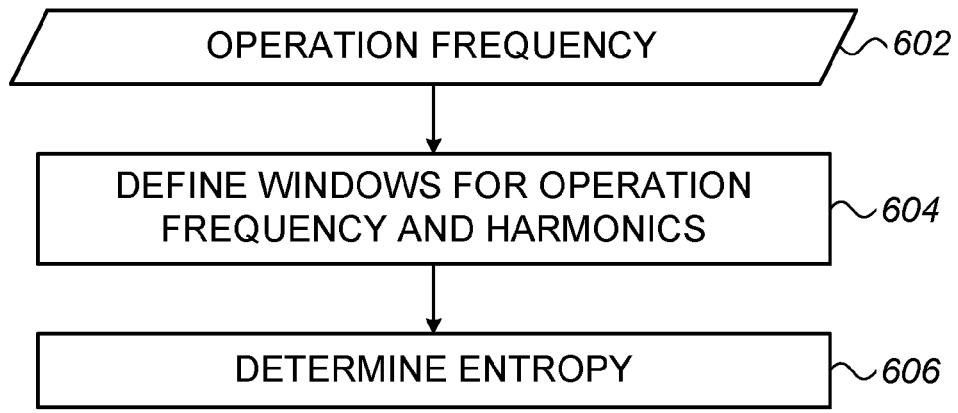
FIG. 6 is a flowchart of a method for determining a regularity parameter value, in accordance with an embodiment of the invention.

FIG. 6 is a flowchart of a method for determining a regularity parameter, in accordance with an exemplary embodiment of the invention. The regularity parameter can be used to evaluate the existence of broken gears instead of, or in addition to, the SDP around the cycle frequency. In calculating the regularity parameter, an indication of an estimation of the cycle frequency of machine 22 is received (602) by acoustic signal monitor 26. Frequency windows are defined (604) around the cycle frequency and one or more of its harmonics, in a frequency spectrum of the collected signals. An entropy is determined (606) for each of the windows. A low entropy value for one or more of the windows is indicative of a large difference between the frequency powers in the window. In machines based on gears, for example, the low entropy value may be indicative of a breakage of one of the gear teeth, causing the existence of a high power frequency around the cycle frequency and/or one or more of its harmonics.

It is noted that instead of determining (606) an entropy of the extracted amplitudes, any other measure of the regularity of the power of the frequencies in the windows may be used, such as the weights discussed above with reference to FIG. 3.

The windows are optionally sufficiently large to encompass the cycle frequency in case the estimate was inaccurate and to encompass frequencies adjacent the cycle frequency which have a substantially different power level, when noise at the cycle frequency exists. In some embodiments, the windows have a frequency band of between about 10-100 HZ, although larger or smaller windows may be used when appropriate.

Figure 7:
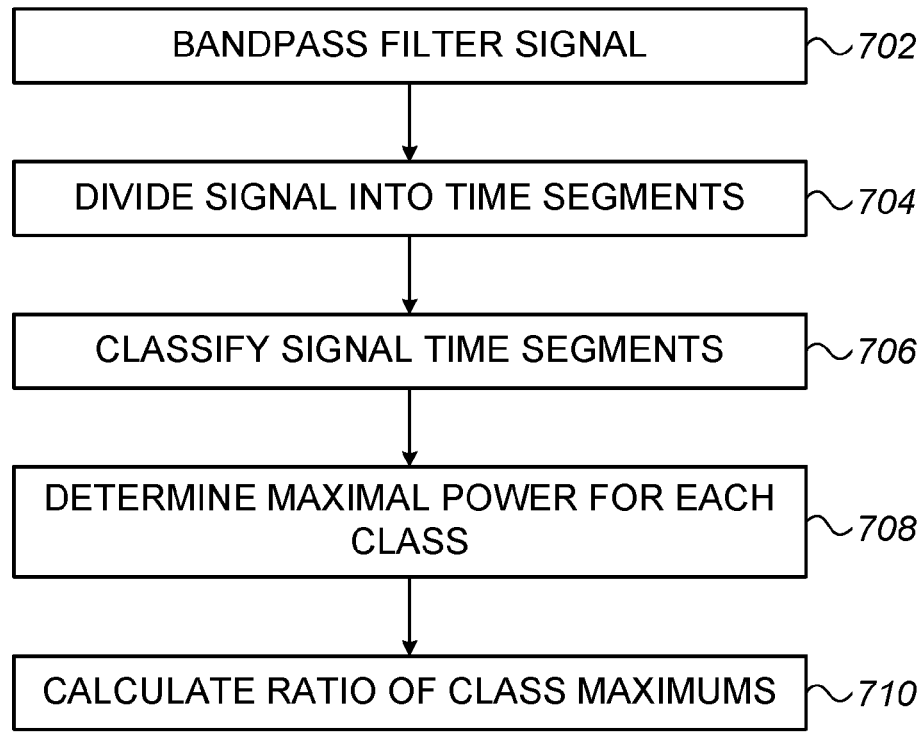
FIG. 7 is a flowchart of a method for determining an operation ratio parameter value, in accordance with an exemplary embodiment of the invention.

FIG. 7 is a flowchart of a method for determining an operation ratio parameter, in accordance with an embodiment of the invention. The operation ratio parameter is indicative of the ratio of the noise between times at which machine 22 is operating on material and times in which machine 22 is operating on neutral.

The method optionally begins with filtering (702) the received signal by a bandpass filter, so that only frequencies in a window expected to clearly differentiate between work operation and neutral operation are taken into consideration. Monitor 26 then divides (704) the filtered acoustic signal into small time segments.

Each time segment of the signal is classified (706) to either neutral or work operation, according to analysis of the acoustic signals. A maximal power of the signal in the segments classified as neutral operation is determined (708) and also a maximal power of the signal in the segments classified as work operation is determined (708). The ratio between the maximal neutral operation power and the maximal work operation power is optionally calculated (710).

Optionally, the classification (706) is performed using any suitable voice activity detection (AVD) method known in the art. In the above description, the maximal work operation power is based on the entire signal in segments classified as from work periods. In other embodiments, the signal from the work periods is processed to remove the part of the signal due to the idle operation of machine 22, for example using a voice activity detection (AVD) method. The calculated (710) ratio is calculated in these embodiments as the ratio between the maximal neutral operation power and the maximal work operation power, after removal of the neutral operation signal.

In various machines, the ratio is indicative of the operation of the machine. For example, in a saw, the calculated ratio was determined by the applicant of the present application to be indicative of a deflection of the saw blade, such that a relatively high ratio may require a maintenance act. When the saw is intended to move without cutting material, the saw is not supposed to come in contact with the material being cut, and the ratio is expected to be relatively low. If, however, the orientation of the machine is inaccurate, even when moving in the neutral operation mode, the saw comes in contact with the material being cut, and the ratio is expected to be closer to 1.

Referring in more detail to the filtering (402), in some embodiments of the invention, in a test session, the operation ratio parameter is calculated for a plurality of different frequency windows and a window which produces a highest ratio is selected. Alternatively or additionally, in the test session, measurements are made in both a high quality operation state and a low quality operation state and a frequency window which provides a best distinction in the calculated ratio between the high quality operation state and the low quality operation state is used.

The test station may be performed on the actual machine, or may be performed on a test machine similar to the machines for which the ratio is calculated.

In one embodiment, a frequency band between 14 KHz and 20 KHz is used. It is noted, however, that other frequency bands may be used in other embodiments.

As to dividing the signal into small time segments, in some embodiments, the time segments are smaller than milliseconds, smaller than 1 millisecond or even smaller than 0.1 milliseconds. It is noted, however, that to avoid intensive calculations, the time segments may be greater than 1 millisecond or even greater than 10 milliseconds.

Referring in detail to presenting (206) the determined parameters, in some embodiments of the invention, acoustic signal monitor 26 repeatedly determines the parameter values periodically and the values are displayed graphically in a manner allowing the operator to appreciate trends in the values. Alternatively or additionally, during a training session, acoustic signal monitor 26 determines a correlation between the values of one or more of the determined parameters and a time until a maintenance act, such as replacing a gear, is due. The display, optionally presents the determined parameter values along with the prediction time. Possibly, the prediction is displayed using a color code or any other suitable graphic presentation.

In some embodiments of the invention, the parameters are presented (206) along with an indication of a desired range of values and/or a color coding of whether the value is good.

The rate at which the parameter values change is optionally also presented. The rate may displayed along with comparative values from a training session of the machine or of other similar machines.

As discussed above, one or more parameters are compared to respective allowed ranges, thresholds or reported values. In some embodiments, monitor 26 determines whether a combination of parameter values is reasonable. For example, for a first operation rate machine 22 is expected to operate with an acoustic amplitude within a first range, while for a second operation rate of machine 22, a different reasonable acoustic amplitude range is set.

As mentioned above, in some embodiments, acoustic signal monitor 26 compares (212) the determined parameters to feedback from controller 28. Such comparison may indicate problems with the controller 28 and/or may serve as a sanity check for acoustic signal monitor 26.

In some embodiments, the acoustic signals and/or one or more parameters derived therefrom are analyzed using a machine learning classifier, e.g., a neural network. Optionally, during a training session, the classifier is fed with acoustic signals and corresponding known machine attributes. Thereafter, the classifier classifies unknown machines according to received acoustic signals.

For example, for classification of a saw, the classifier is optionally trained to determine, from provided acoustic signals, one or more of the parameters: Saw type, saw size, number of teeth on saw, type of material being cut by the saw, width of material being cut by the saw, profile of material being cut by the saw, diameter of material being cut by the saw, and degree of wear of blade. During the training session, the machine is operated until a maintenance act is required and thereafter the values acquired during the training are associated with the time from their determination to the time of the maintenance act.

It will thus be appreciated that the embodiments described above are cited by way of example, and that the following claims are not limited to what has been particularly shown and described hereinabove. Rather, the scope includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method of monitoring a machine, comprising:
acquiring, by an acoustic sensor, acoustic signals from a vicinity of a machine, while the machine is operative;
calculating, by a processor, a frequency spectrum of a segment of the acquired acoustic signals;
determining boundaries of a frequency band to be analyzed;
extracting, from the calculated frequency spectrum, a base frequency window in the determined boundaries, and one or more harmonics windows of harmonics of the determined boundaries;
determining for each of the base and harmonic windows a weight based on a distribution of values of frequencies in the windows;
calculating a parameter of operation of the machine as a function of a weighted sum of the base and harmonic windows; and
providing feedback on the operation of the machine, responsive to the calculated parameter, on a display coupled to the processor.

2. The method of claim 1, comprising generating an alert, responsive to a determination that the calculated parameter is outside a predefined range of values for the parameter.

3. The method of claim 1, comprising generating an alert, responsive to a determination that the calculated parameter is different than a corresponding value reported by a controller of the machine.

4. The method of claim 1, wherein calculating the operation parameter comprises determining a frequency in the weighted sum of the windows having a maximal power.

5. The method of claim 1, wherein calculating the operation parameter comprises determining a ratio between power in a segment around a given frequency in the weighted sum of the windows and a measure of power outside the segment.

6. The method of claim 1, wherein determining a weight for each window comprises determining a frequency-domain entropy of the window.

7. The method of claim 1, wherein further comprising determining a time until a required maintenance of the machine, as a function of the calculated parameter.

8. The method of claim 1, further comprising automatically changing an operation state of the machine responsive to the calculated parameter.

9. The method of claim 5, wherein determining the ratio comprises calculating a numerator of the ratio as a power in frequency segments around an operation frequency of the machine and one or more harmonics of the operation frequency.

10. The method of claim 9, wherein the operation frequency comprises a frequency corresponding to a time period of a single cog of a gear of the machine.

11. The method of claim 10, wherein providing the feedback comprises automatically providing an estimate of a time to a required replacement of the gear.

12. The method of claim 9, wherein the operation frequency comprises a frequency corresponding to an entire cycle of a gear of the machine.

13. The method of claim 12, wherein providing the feedback comprises determining that the ratio is in a predetermined range and providing an alert of a broken gear cog responsively to the determining.

14. The method of claim 5, wherein determining the ratio comprises calculating a denominator of the ratio as a power of the entire frequency spectrum.

15. The method of claim 5, wherein determining the ratio comprises calculating a denominator of the ratio as a power of the frequency spectrum not included in the segments.

16. The method of claim 5, wherein calculating the frequency spectrum comprises extracting a sample of a given duration from the acquired signals and calculating the frequency spectrum from the extracted sample.

17. The method of claim 16, wherein extracting the sample comprises extracting at times defined by an electrical timing signal from the machine.

18. An acoustic machine monitor, comprising:
an acoustic sensor for acquiring acoustic signals from a vicinity of a machine, while the machine is operative; and
a processor configured to calculate a frequency spectrum of a segment of the acquired acoustic signals, to determine boundaries of a frequency band to be analyzed, to extract from the calculated frequency spectrum, a base frequency window in the determined boundaries, and one or more harmonics windows of harmonics of the determined boundaries, to determine for each of the base and harmonic windows a weight based on a distribution of values of frequencies in the windows, to calculate a parameter of operation of the machine as a function of a weighted sum of the base and harmonic windows, and to provide feedback on the operation of the machine, responsive to the calculated parameter.

19. The monitor of claim 18, wherein the processor is configured to generate an alert, responsive to a determination that the calculated parameter is outside a predefined range of values for the parameter.

* * * * *